United States Patent [19]

Graham

[11] 4,013,730
[45] Mar. 22, 1977

[54] PROCESS FOR THE PREPARATION OF MONOCHLOROTOLUENE

[75] Inventor: John C. Graham, Warren, Mich.

[73] Assignee: Hooker Chemicals & Plastics Corporation, Niagara Falls, N.Y.

[22] Filed: Aug. 1, 1975

[21] Appl. No.: 601,691

[52] U.S. Cl. .............................. 260/650 R; 252/439
[51] Int. Cl.² ......................................... C07C 25/04
[58] Field of Search ............................... 260/650 R

[56] References Cited

UNITED STATES PATENTS 3,226,447  12/1965  Bing et al. ..................... 260/650 R Primary Examiner—D. Horwitz
Attorney, Agent, or Firm—Peter F. Casella; William J. Crosetta, Jr.; Arthur S. Cookfair

[57] ABSTRACT

A process for the chlorination of toluene comprises reacting toluene with chlorine in the presence of a catalyst system comprising a Lewis acid catalyst and a co-catalyst selected from the group consisting of diphenyl selenide and aluminum selenide. The monochlorotoluene product obtained is characterized by a substantially reduced ratio of orthochlorotoluene to parachlorotoluene.

14 Claims, No Drawings

PROCESS FOR THE PREPARATION OF MONOCHLOROTOLUENE

BACKGROUND OF THE INVENTION

This invention relates to a process for the chlorination of toluene to form a monochlorotoluene product having a substantially reduced proportion of orthochlorotoluene to parachlorotoluene.

It is known that the presence of an alkyl group on an aromatic ring tends to direct incoming substituents in electrophilic aromatic substitution reactions to the ortho- and para- positions of the aromatic ring. Thus, for example, in the chlorination of toluene, the usual product is a mixture of orthochlorotoluene and parachlorotoluene. The presence of two ortho- ring positions and only a single para- ring position results in the formation of a considerable excess of orthochlorotoluene over parachlorotoluene, often in proportions approximating the theoretical 2:1 ratio of orthochloro:-parachloro isomer.

The chlorination of toluene is frequently carried out in the presence of a Lewis acid catalyst such as ferric chloride or antimony chloride. The monochlorotoluene produced in such a process will generally contain a significant excess of orthochlorotoluene over parachlorotoluene. From a commercial point of view, the production of orthochlorotoluene in such a process is undesirable since little, if any, demand for that isomer exists. On the other hand, the parachloro isomer is readily marketable and is a commercially valuable product. Thus, the orthochlorotoluene must be stored, disposed of in a non-polluting manner or recycled by hydrogenation to toluene. Such measures markedly reduce the efficiency and significantly increase the expense of the toluene chlorination process. It will be apparent therefore that it is desirable, from a commercial point of view, to chlorinate toluene under conditions which minimize the formation of orthochlorotoluene and maximize the formation of parachlorotoluene. Processes to achieve this purpose are known in the prior art. Thus, for example, it is known from U.S. Pat. No. 1,946,040 that when alkylbenzenes are reacted with chlorine, the yield of parachlorinated product is improved with the aid of a mixed catalyst comprising sulfur and antimony trichloride and optionally, iron or lead. In British Pat. No. 1,153,746 (1969) it is disclosed that in the chlorination of toluene in the presence of a ring chlorination catalyst, such as iron, ferric chloride, antimony chloride and the like, the ratio of orthochloro to parachloro isomers produced may be lowered by the presence of an organic sulfur compound such as thiophene, hexadecylmercaptan, dibenzothiophene or the like. Furthermore, in British Pat. No. 1,163,927 (1969) it is disclosed that the proportion of parachlorotoluene produced may be improved when toluene is chlorinated in the presence of elemental sulfur or an inorganic sulfur compound and a ring-chlorination catalyst such as ferric chloride, aluminum chloride, antimony chloride, and the like. The processes thus disclosed provide a substantial improvement in the yield of parachlorotoluene. Nevertheless, it will be apparent that still further improvement in the yield of parachlorotoluene is desirable. In U.S. Pat. No. 3,226,447, issued Dec. 28, 1965 to Bing et al, it is disclosed that in the substituted - chlorination of benzenes and toluene by chlorine, the ratio or ortho isomer to para isomer in the chlorinated product may be lowered when the reaction is carried out in the presence of an iron, aluminum, or antimony halide catalyst and a co-catalyst which is an organic sulfur compound wherein the sulfur is divalent. Examples of such co-catalyst include various mercaptans, mercapto-aliphatic carboxylic acids, aliphatic thiocarboxylic acids, alkyl sulfides, alkyl disulfides, thiophenols, aryl sulfides, aryl sulfides, aryl disulfides and the like containing divalent sulfur. The use of such co-catalysts in the chlorination of toluene produces a product wherein the ratio of orthochlorotoluene to parachlorotoluene is 1.2, indicating a considerable improvement over the ortho to para isomer ratio achieved in the absense of the co-catalyst. However, it will be apparent that even a 1.2 ratio of ortho to para isomer represents a considerable economics disadvantage in the production of substantial amounts — greater than 50 percent of the monochlorotoluene mixture — of the unwanted ortho isomer. Thus, it will be apparent that a considerable commercial benefit is to be derived from a still further lowering of the ortho to para isomer ratio.

Accordingly, it is an object of this invention to provide a process for the chlorination of toluene whereby the proportion of orthochlorotoluene to parachlorotoluene product is substantially reduced. It is a further object to provide a novel catalyst system capable of exerting a paradirecting effect in the chlorination of toluene. Other objects and advantages will become apparent from the details and examples provided herein below.

SUMMARY OF THE INVENTION

It has now been found that in the process for the preparation of monochlorotoluene by reaction of toluene with chlorine, a substantial lowering of the ratio of orthochlorotoluene to parachlorotoluene product is obtained when the process is carried out in the presence of a catalyst system comprising a Lewis acid catalyst and a co-catalyst selected from the group consisting of diphenyl selenide and aluminum selenide.

A wide variety of known Lewis acid catalysts may be employed in the process of the present invention. Preferred catalysts for this purpose are compounds of antimony, lead, iron, molybdenum and aluminum, including for example, the halides, oxyhalides, oxides, sulfides, sulfates, carbonyls and elemental form of these elements and mixtures of such compounds and most preferably the chlorides, oxychlorides, and oxides and elemental forms of antimony and iron. Typical of the catalysts which may be employed in the process of this invention are aluminum chloride. antimony trichloride, antimony pentachlofide, antimony trioxide, antimony tetraoxide, antimony pentaoxide, antimony trifluoride, antimony oxychloride, molybdenum hexacarbonyl, ferric chloride, ferrous chloride, ferrous sulfate, ferric oxide, iron pentacarbonyl, iron metal, and the like.

The amount of catalyst system employed is not critical and may vary considerably. Typically, the amount of catalyst system is in the range of about 0.01 to about 10.0 percent by weight and preferably from about 0.1 to about 2.0 percent by weight based on the weight of toluene. The proportion of Lewis acid catalyst to selenide co-catalyst may vary considerably but will typically be within a weight ratio of catalyst:co-catalyst of about 10:1 to about 1:10. Preferably the catalyst system will contain a weight ratio of catalyst:co-catalyst of from about 3:1 to about 1:3.

The chlorination reaction may be carried out over a wide range of temperatures, for example from room temperature (25° C) or below to 100° Celsius or higher. Normally, the reaction temperature is maintained in a range of about 25° to about 75° and preferably about 40° to 65° Celsius. The chlorination is preferably carried out at atmospheric pressure although subatmospheric or superatmospheric pressures may be employed if desired.

In accordance with the preferred mode of carrying out the process of this invention, toluene is charged to a reaction vessel together with a catalytic amount of the Lewis acid catalyst and selenide co-catalyst. The reaction mixture is maintained at about 25° to 75° Celsius with agitation, while chlorine is introduced slowly until about fifty to one-hundred percent of the and preferably seventy to ninety-five percent of the stoichiometric amount required for monochlorination has been added. The reaction mixture is then purged, for example with air or nitrogen, to remove hydrogen chloride and residual chlorine. The reaction product may then be purified if desired, to separate it into its component parts by known techniques such as fractional crystallization, distillation or the like.

When, in accordance with this invention, toluene is reacted with chlorine in the presence of a catalyst system comprising a Lewis acid and diphenyl selenide or aluminum selenide, a monochlorotoluene product is obtained wherein the ratio of orthochloro:parachloro isomer is appreciably less than that obtained when toluene is reacted with chlorine in the presence of the Lewis acid catalyst alone. Furthermore the monochlorination, in accordance with this invention, may be carried to greater than 90 percent of completion without the formation of significant amounts of ring polychlorinated products. The monochlorination of toluene to high levels of conversion without the formation of excessive amounts of such undesirable by-products constitutes a distinct advantage of the present invention. Thus, for example, a manufacturer of monochlorotoluene, using only the Lewis acid catalysts of the prior art is normally faced with a choice between stopping the reaction at a level substantially below that required for stoichiometric monochlorination, or carrying the chlorination reaction to near completion. In the first choice the formation of unwanted ring polychlorinated products is avoided at the cost of having to recover the unreacted toluene while in the latter alternative, ring polychlorinated products form, necessitating their subsequent separation and disposal. Normally, the first of these possible routes is taken. The process of this invention allows the toluene monochlorination to be carried closer to stoichiometric completion without the formation of significant amounts of undesirable polychlorinated products.

The following examples will serve to further illustrate the invention and the manner in which it may be carried out. In the examples, as well as elsewhere in the specification and claims, unless otherwise indicated, all parts and percentages are by weight and temperatures are in degrees Celsius. Product analyses were obtained by gas chromatographic methods.

EXAMPLE 1

A mixture of 300 parts of toluene, 3.0 parts of diphenyl selenide and 2.1 parts of ferric chloride was charged to a reaction vessel. This mixture was heated to 50° C and maintained at about that temperature while 110 parts of chlorine was introduced slowly over a period of about 4 hours. The reaction mixture was then purged with nitrogen to remove hydrogen chloride and residual chlorine. Analysis of the reaction product was as follows:
Toluene: 6.7 Percent
Orthochlorotoluene: 44.9 Percent
Parachlorotoluene: 48.4 Percent
Ortho:Para Ratio: 0.93

EXAMPLE 2

The procedure of Example 1 was repeated except that the reaction mixture consisted of 92.1 parts of toluene, 1.2 parts of aluminum selenide, and 1.0 parts of ferric chloride, and 43 parts of chlorine was introduced over a three hour period. Analysis of the reaction mixture established it to have the following composition:
Toluene: 40.0 Percent
Orthochlorotoluene: 31.0 Percent
Parachlorotoluene: 28.5 Percent
Ortho:Para Ratio: 1.10

EXAMPLE 3

The procedure of Example 1 was repeated except that the reaction mixture consisted of 92.1 parts of toluene, 1.0 parts of diphenyl selenide and 1.0 parts of antimony chloride and 36 parts of chlorine was introduced over about a three hour period. Analysis of the reaction mixture established it to have the following composition:
Toluene: 50.3 Percent
Orthochlorotoluene: 25.2 Percent
Parachlorotoluene: 24.4 Percent
Ortho:Para Ratio: 1.03

EXAMPLE 4

The procedure of Example 3 was repeated except that in place of 1.0 parts of antimony chloride there was substituted 0.7 parts of ferric chloride. Analysis of the reaction product established it to have a composition as follows:
Toluene: 27.3 Percent
Orthochlorotoluene: 34.3 Percent
Parachlorotoluene: 38.4 Percent
Ortho:Para Ratio: 0.89

Examples 5 and 6 below are presented for purposes of comparison and to demonstrate the criticality of the catalyst compositions of this invention and the unpredictability of such catalyst compositions.

EXAMPLE 5

The procedure of Example 1 was repeated except that the reaction mixture consisted of 92.1 parts of toluene, 0.6 parts of diethylselenide, 1.0 parts of antimony chloride and approximately 35 parts of chlorine was introduced into the reaction mixture over a period of about three hours. Analysis of the reaction product established it to be as follows:
Toluene: 50.7 Percent
Orthochlorotoluene: 32.5 Percent
Parachlorotoluene: 16.8 Percent
Ortho:Para Ratio: 1.93

EXAMPLE 6

The procedure of Example 1 was repeated except that the reaction mixture consisted of 92.1 parts of toluene, 1.0 parts of diphenyl telluride, and 0.57 parts of ferric chloride and 36 parts of chlorine was introduced over a period of about three hours. Analysis of the reaction product established it to be as follows:

Toluene: 50.5 Percent
Orthochlorotoluene: 31.9 Percent
Parachlorotoluene: 17.5 Percent
Ortho:Para Ratio: 1.82

What is claimed is:

1. A process for the preparation of parachlorotoluene which comprises reacting toluene with chlorine in the presence of about 0.01 to about 10.0 percent by weight of a catalyst system comprising a Lewis acid catalyst and a co-catalyst selected from the group consisting of diphenyl selenide and aluminum selenide.

2. A process according to claim 1 wherein the Lewis acid catalyst is ferric chloride.

3. A process according to claim 2 wherein the co-catalyst is diphenyl selenide.

4. A process according to claim 2 wherein the co-catalyst is aluminum selenide.

5. A process according to claim 2 wherein the catalyst system is present in an amount of about 0.01 to about 10.0 percent by weight based on the weight of toluene, and the weight ratio of catalyst:co-catalyst is about 10:1 to about 1:10.

6. A process according to claim 1 wherein the Lewis acid catalyst is antimony chloride.

7. A process according to claim 6 wherein the co-catalyst is diphenyl selenide.

8. A process according to claim 6 wherein the catalyst system is present in an amount of about 0.01 to about 10.0 percent by weight based on the weight of toluene, and the weight ratio of catalyst:co-catalyst is about 10:1 to about 1:10.

9. A process according to claim 1 which comprises reacting toluene with chlorine at a temperature of about 25° to about 75° Celsius in the presence of about 0.1 to about 2.0 percent by weight, based on the weight of toluene, of a catalyst system comprising a catalyst selected from the group consisting of ferric chloride and antimony chloride, and a co-catalyst selected from the group consisting of diphenyl selenide and aluminum selenide, the weight ratio of catalyst:co-catalyst being about 3:1 to about 1:3.

10. A process according to claim 9 wherein the Lewis acid catalyst is ferric chloride.

11. A process according to claim 9 wherein the Lewis acid catalyst is antimony chloride.

12. The process of claim 1 wherein said Lewis acid catalyst is at least one of aluminum chloride, antimony trichloride, antimony pentachloride, antimony trioxide, antimony tetraoxide, antimony pentaoxide, antimony trifluoride, antimony oxychloride, molybdenum hexacarbonyl, ferric chloride, ferrous chloride, ferrous sulfate, ferric oxide, iron pentacarbonyl and iron metal.

13. The process of claim 1 wherein toluene is reacted with chlorine at a temperature range from below room temperature to above 100° Celsius.

14. The process of claim 13 wherein said temperature range is about 25° to about 75° Celsius.

* * * * *